United States Patent
Pandey et al.

(10) Patent No.: US 10,076,550 B2
(45) Date of Patent: Sep. 18, 2018

(54) SYNERGISTIC PHARMACEUTICAL COMPOSITION FOR GASTROINESTINAL DISORDERS

(71) Applicant: COUNCIL OF SCIENTIFIC & INDUSTRIAL RESEARCH, New Delhi (IN)

(72) Inventors: Garima Pandey, Lucknow (IN); Chandana Venkateswara Rao, Lucknow (IN); Om Prakash Sidhu, Lucknow (IN); Ajay Kumar Singh Rawat, Lucknow (IN); Chandra Shekhar Nautiyal, Lucknow (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 444 days.

(21) Appl. No.: 14/547,296

(22) Filed: Nov. 19, 2014

(65) Prior Publication Data

US 2015/0374768 A1 Dec. 31, 2015

(30) Foreign Application Priority Data

Jun. 25, 2014 (IN) .......................... 1698/DEL/2014

(51) Int. Cl.
| | |
|---|---|
| *A61K 36/185* | (2006.01) |
| *A61K 31/194* | (2006.01) |
| *A61K 31/201* | (2006.01) |
| *A61K 9/00* | (2006.01) |
| *A61K 9/16* | (2006.01) |

(52) U.S. Cl.
CPC .......... *A61K 36/185* (2013.01); *A61K 9/0095* (2013.01); *A61K 9/1652* (2013.01); *A61K 31/194* (2013.01); *A61K 31/201* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 2002/0010211 A1* | 1/2002 | Obukowicz | A61K 31/202 514/549 |
| 2011/0097401 A1* | 4/2011 | Phillips | A61K 9/0053 424/479 |
| 2012/0015412 A1* | 1/2012 | Hu | C07C 227/06 435/128 |
| 2012/0065266 A1* | 3/2012 | Fujita | A61K 9/1652 514/565 |

FOREIGN PATENT DOCUMENTS

| | | | |
|---|---|---|---|
| IN | 200501523 | * | 3/2006 |
| IN | 241754 | | 7/2010 |
| IN | 243944 | | 11/2010 |
| WO | WO2005016332 | * | 2/2005 |

OTHER PUBLICATIONS

Valentina, P. et al., Synthesis, structure and biological activity of nitroxide malonate methanofullerenes, Org. Biomol. Chem., 2007, 5, pp. 976-981.
Vickery, HB, et al, The metabolism of the organic acids of tobacco leaves :XII. Effect of culture of excised leaves on solutions of malonate at pH 4 to pH 7, Journal of Biological Chemistry, 1957, 225, pp. 629-640.
Villamor, E, et al, Long-chain n-6 polyunsaturated fatty acids in breast milk decrease the risk of HIV transmission through breastfeeding 1-3, The American Journal of Clinical Nutrition, 2007, 86, pp. 862-9.
Henry, G E, Antioxidant and cyclooxygenase activities of fatty acids found in food. J. Agric. Food Chem., 2002, 50: pp. 2231-2223.
Pierce, NF, et al., Effects of prostaglandins, Theophylline and cholera exotoxin upon transmucosal water and electrolyte movement in canine jejunum, Gastroenterology, 1971; 60, pp. 22-32.
Galveg, J., et al., Anti-diarrheic activity of euphorbia hirta extract and isolation of an active flavonoid constituent, Plantamedica, 1993; 59, pp. 333-336.
Alkofahi, A., et al., Pharmacological screening of the anti-ulcerogenic effects of some Jordanian Medicinal Plants in rats, J. Ethnopharmacol, 1999, 65: pp. 341-345.
Peskar, BM, et al., Role of prostaglandins in gastroprotection, 1998, Dig. Dis. Sci., 43: 523-529.
Babbar N., et al., Induction of spermidine/spermine N1-acetyltransferase (SSAT) by aspirin in Caco-2 colon cancer cells, Biochem J, 2006, 394 (Pt 1), pp. 317-324.
Patel, AV, et al., Antiulcer activity and the mechanism of action of magaldrate in gastric ulceration models of rat, Indian J Physiol Pharmacol, 2000, 44, pp. 350-354.
Akhtar, AH, et al. Anti-ulcerogenic evaluation of the methanolic extracts of some indigenous medicinal plants of Pakistan in aspirin-ulcerated rats, J Ethnopharmacol., 1995, 46, pp. 1-6.
Atta, AH, et al., Antiulcerogenic effect of some plant extracts, Natural Product Radiance, 2005, 4, pp. 258-263.
Jamal, A., Gastroprotective effect of cardamom, Elettaria cardamomum Maton fruits in rats, J Ethnopharmacol, 2006, 103, pp. 149-153.
Konturek, SJ, et al., Role of leukotrienes in acute gastric lesions by ethanol, taurocholate, aspirin, platelet activating factor and stress in rats, Dig Dis Sci, 1988, 33, pp. 806-813.

(Continued)

*Primary Examiner* — Chris R Tate
*Assistant Examiner* — Randall Winston
(74) *Attorney, Agent, or Firm* — Andrews Kurth Kenyon LLP

(57) ABSTRACT

The present invention relates to a mainly herbal composition comprising *Terminalia bellerica* fruits (1-5% w/w) more particularly the extract of dried fruits. The composition further has exogenously added malonic acid, glutamic acid, eicosenoic acid and linolenic acid. The composition of present invention is useful in treatment and control of gastro intestinal problems like diarrhea, dysentery, ulcers etc. and used as an oral dosage form.

6 Claims, No Drawings

(56) References Cited

OTHER PUBLICATIONS

Wallace JL, Mechanisms of protection and healing: current knowledge and future research, Am J Med, 2001, 110, pp. 19-23.
Robert, A., et al., Cytoprotection by prostaglandins in rats Prevention of gastric necrosis produced by alcohol, HCl, NaOH, hypertonic NaCl and thermal injury, Gastroenterology, 1979, 77, pp. 433-443.
Gazzieri, D., et al., Substance P released by TRPVI-expressing neurons produces reactive oxygen species that mediate ethanol-induced gastric injury, Free Radic Biol Med, 2007, 43, pp. 581-589.
Hollander, D., et al. Protective effect of sucralfate against alcohol-induced gastric mucosal injury in the rat, Gastroenterology, 1985, 88, pp. 366-374.
Qiu BS, et al., Tthe influence of chronic nicotine treatment on stress-induced gastric ulceration and emptying rate in rats, Experientia, 1992, 48, pp. 389-391.
Brown, JF, et al., Nitric oxide generators and cGMP stimulate mucus secretion by rat gastric mucosal cells, Am J Physiol 1993, 265, pp. G418-422.
Brown, JF, et al., Nitric oxide donors increase mucus gel thickness in rat stomach, Eur J Pharmacol, 1992, 223, pp. 103-104.
Qiu, BS, et al., Effects of chronic nitric oxide synthase inhibition in cold-restraint and ethanol-induced gastricmucosal damage in rats, Digestion, 1996, 57, pp. 60-66.
Shailendra, P., et al., International Journal of Pharmaceutical & Biological Archives, 2012, 3(3), pp. 466-473.
Gautam V., et al., Exporting Indian healthcare (Export potential of Ayurveda and Siddha products and services). Road Beyond Boundaries (The Case of Selected Indian Healthcare Systems)Export-Import Bank of India, Mumbai, 2003. pp. 14-54.
Sharma, H., et al., Principles of pharmacology by Paras publication, Hyderabad, India., 2008, pp. 387-390.
Nadkami KM (2002). Indian Meteria Medica, Published by Ramdas Bhatkal for Popular Prakashan Pvt. Ltd. Mumbai 01: 1202-1205.

\* cited by examiner

SYNERGISTIC PHARMACEUTICAL COMPOSITION FOR GASTROINESTINAL DISORDERS

This application claims priority from Indian Patent Application No. 1698/DEL/2014 filed in India on Jun. 25, 2014, the contents of which are incorporated herein by reference.

FIELD OF INVENTION

The present invention relates to a synergistic pharmaceutical composition for gastrointestinal disorders. The present invention particularly relates to herbal composition comprising *Terminalia bellerica* fruits, more particularly the extract of fruits and exogenously added malonic acid, glutamic acid, eicosenoic acid and linolenic acid which can be used for the effective cure of gastro intestinal problems. The composition of present invention is useful in treatment and control of gastro intestinal problems and used as an oral dosage form.

BACKGROUND OF THE INVENTION

Diarrhea is the condition of having three or more loose or liquid bowel movements per day (World Health Organization). It is a common cause of death in developing countries and the second most common cause of infant deaths worldwide. The loss of fluids through diarrhea can cause dehydration and electrolyte disturbances such as potassium deficiency or other salt imbalances. In 2009 diarrhea was estimated to have caused 1.1 million deaths in people aged 5 and over and 1.5 million deaths in children under the age of 5. Oral rehydration solutions (ORS) with modest amounts of salts and zinc tablets are the treatment of choice and have been estimated to have saved 50 million children in the past 25 years. (WHO). Osmotic diarrhea means that something in the bowel is drawing water from the body into the bowel. A common example of this is "dietetic candy" or "chewing gum" diarrhea, in which a sugar substitute, such as sorbitol, is not absorbed by the body but draws water from the body into the bowel, resulting in diarrhea. Secretory diarrhea occurs when the body is releasing water into the bowel when it's not supposed to. Many infections, drugs, and other conditions cause secretory diarrhea. Exudative diarrhea refers to the presence of blood and pus in the stool. This occurs with inflammatory bowel diseases, such as Crohn's disease or ulcerative colitis, and several infections. The most common cause of diarrhea is a virus that infects the gut. The infection usually lasts for two days and is sometimes called "intestinal flu" or "stomach flu." Diarrhea may also be caused by:

Infection by bacteria (the cause of most types of food poisoning), infections by other organisms, eating foods that upset the digestive system, allergies to certain food, medications, radiation therapy, diseases of the intestines (Crohn's disease, ulcerative colitis), malabsorption (where the body is unable to adequately absorb certain nutrients from the diet), hyperthyroidism, some cancers, laxative abuse, alcohol abuse, digestive tract surgery, diabetes Recently, the World Health Organization estimated that 80% of the people worldwide rely on herbal medicines for some part of their primary health care. In Germany, about 600-700 plant based medicines are available and are prescribed by some 70% of German physicians. In the past 20 years in the United States, public dissatisfaction with the cost of prescription medications, combined with an interest in returning to natural or organic remedies, has led to an increase in herbal medicine use. Millions of Indians also use herbal drugs regularly, as spices, home-remedies, health foods as well as over-the-counter (OTC) as self-medication or also as drugs prescribed in the non-allopathic systems (Gautam V., Raman R. M. V., Ashish K. Exporting Indian healthcare (Export potential of Ayurveda and Siddha products and services). *Road Beyond Boundaries* (*The Case of Selected Indian Healthcare Systems*) Export-Import Bank of India; Mumbai: 2003. pp. 14-54). Herbal based drugs are known to have no adverse effects and cure the diseases in a holistic manner. They treat the cause and not merely the symptoms of disease as they have many active constituents which act in synergy. Under the present scenario the development of a herbal based composition for effective cure of gastrointestinal diseases is required.

*Terminalia bellerica* (Roxb):Family: Combretaceae

Botanical description and phytoconstituents: *T. bellerica* also referred to as, Beleric Myrobalan in English, Bibhitaki in Sanskrit, locally known as Bahera in India, has been used for centuries in the Ayurveda, a holistic system of medicine originating from India. It is a large deciduous tree found throughout India, in areas up to an altitude of 1,000 meters. The tree takes a height of 30 meters, while the bark is brownish grey in color. The alternate, broadly elliptic leaves are clustered towards the end of the branches. They are 10 to 12 cm in length and 7 to 14 cm in breadth. The simple, solitary flowers are in auxiliary spikes, with offensive odor. They blossom in the month of May. The fruits are ovoid grey drupes and the kernels are sweet. The tree is found in abundance in Madhya Pradesh, Uttar Pradesh, Punjab and Maharashtra. The dried fruit is used for medicinal purposes (Indian Herbal Pharmacopoeia, 2002). It is found growing wild throughout the Indian subcontinent, Sri Lanka, and SE Asia, upto 1200 meters in elevation, in a wide variety of ecologies. (Nadkami K M, 2002, Indian Meteria Medica, Published by Ramdas Bhatkal for Popular Prakashan Pvt. Ltd. Mumbai 01: 1202-1205) Glucoside bellericanin (The Ayurvedic Pharmacopoeia of India, 2001) gallo-tannic acid, coloring matter, resins and a greenish yellow oil have been isolated from the *T. bellerica* (Nadkarni K M (2002). Indian Meteria Medica, Published by Ramdas Bhatkal for Popular Prakashan Pvt. Ltd. Mumbai 01: 1202-1205). Ellagic acid, gallic acid, lignans (termilignan and tanni lignan), 7-hydroxy 3'4' 10 (methylene dioxy) flavone and anolignan B are also reported in *T. bellerica* fruits and bark (The Ayurvedic Pharmacopoeia of India, 2001). Tannins, ellagic acid, ethyl gallate, galloyl glucose and chebulaginic acid, phenyllemblin, β-sitosterol, mannitol, glucose, fructose and rhamnose are reported from different parts of the tree (Indian Herbal Pharmacopoeia, 2002; The Ayurvedic Pharmacopoeia of India, 2001).

Medicinal properties: Anthelminthic, antiseptic, astringent, expectorant, laxative, lithotriptic, rejuvenative and tonic. The fruit is one among the triphala formula of ayurveda and is commonly prescribed in treating asthma and biliousness.

Some Indian patents granted, containing *Terminalia bellerica* are, Patent No. 243944, which relates to a novel herbal medicinal composition useful for the treatment of HIV/AIDS; another patent no 241754, which is a composition for the treatment of hemorrhoid.

Malonic acid: Malonic acid (IUPAC systematic name: propanedioic acid) is a dicarboxylic acid with structure $CH_2(COOH)_2$. It is used in the preparation of barbiturates. Malonate nitroxide methanofullerene a derivative of malonic acid enhances the antitumor activity of cyclophosphamide (CPA), which is an anticancer drug (Valentina P.

Gubskaya, Lucia Sh. Berezhnaya, Aidar T. Gubaidullin, Irina I. Faingold, Raisa A. Kotelnikova, Nina P. Konovalova, Vladimir I. Morozov, Igor A. Litvinov and Ildus A. Nuretdinov. Synthesis, structure and biological activity of nitroxide malonate methanofullerenes. Org. Biomol. Chem., 2007, 5, 976-981). It occurs naturally in biological systems, such as legumes and developing rat brains, which indicates that it may play an important role in symbiotic nitrogen metabolism and brain development. It is found in fairly substantial amount in almost eighteen species of leguminous plants (Hubert Bradford Vickery and James K. Palmer. The metabolism of the organic acids of tobacco leaves :XII. Effect of culture of excised leaves on solutions of malonate at pH 4 to pH 7. Journal of Biological Chemistry. 1957, 225:629-640).

Glutamic acid:Glutamic acid (abbreviated asGlu or E) is one of the 20-22 proteinogenic amino acids. It is a non-essential amino acid. Glutamic Acid is an excitatory neurotransmitter for the central nervous system, the brain and spinal cord; important in the metabolism of sugars and fats. It aids in the transportation of potassium into the spinal fluid. Glutamic Acid acts as fuel for the brain. It has been used to help correct personality disorders, in the treatment of epilepsy, mental retardation and muscular dystrophy.

Eicosenoic acid: Eicosenoic acid is also known as gondoic acid. Gondoic acid is reported as one of the fatty acids in breast milk, which contributes to its immuno modulating properties (Villamor Eduardo, Koulinska Irene N, Furtado Jeremy, Baylin Ana, Aboud Said, Manji Karim, Campos Hannia and Fawzi Wafaie W (2007). Long-chain n-6 polyunsaturated fatty acids in breast milk decrease the risk of HIV transmission through breastfeeding. Am. J. Clin. Nutr. 86: 682-289). Anti oxidant property of 11—eicosenoic acid was reported by Henry et al (Henry Geneive E, Momin Rafikali A, Nair Muraleedharan G and Dewitt David. Antioxidant and cyclooxygenase activities of fatty acids found in food. J. Agric. Food Chem. 50: 2231-22232002). Eicosenoic is a common phytoconstituent of coconut, *Eruca sativa*, Flax oil, *Blueperum lanctifolim* etc.

Linolenic acid: Linolenic acid is reported to have antibacterial and anti-inflammatory activity. It is a polyunsaturated fatty acid used in the biosynthesis of arachidonic acid (AA) and thus some prostaglandins. It is found in the lipids of cell membranes. Linolenic acid is abundant in many vegetable oils.

Objectives of Invention

Main objective of the present invention is to provide a synergistic composition based on herbal constituents for the treatment of gastrointestinal disorders.

Another objective of the invention is to provide a process for preparing the composition to form the finished oral product.

SUMMARY OF THE INVENTION

Accordingly, the present invention provides a synergistic composition useful for gastrointestinal disorders comprising *Terminalia bellerica* ranging between 1-5% wt/wt, organic acids 8.5%-15% wt/wt and binder 80%-90.5% wt/wt.

In an embodiment of the invention wherein the composition comprising fruits of *Terminalia bellerica*.

In another embodiment of the invention wherein the composition comprising of dried fruits of *Terminalia bellerica*.

In yet another embodiment of the invention wherein the composition comprising of organic extract of dried fruits of *Terminalia bellerica* preferably 50% ethanolic extract of dried fruits of *Terminalia bellerica* In still another embodiment of the invention wherein the composition wherein organic acids may be selected from a group consisting of malonic acid, eicosenoic acid, linolenic acid and glutamic acid and combination thereof.

In further embodiment of the invention wherein the composition comprising *Terminalia bellerica*(1-5% wt/wt), malonic acid (0.5-2% wt/wt), eicosenoic acid (4-5%) and linolenic acid (24%).

In one more embodiment of the invention wherein the composition is useful for the treatment of gastrointestinal disorders where the gastrointestinal disorders are diarrhea, ulcer, stomach inflammation, dysentery, gastric ulcer, duodenal ulcer, stomach ache, irritable bowel syndrome.

A process for the preparation of composition as claimed in claim 1 comprising: (a) obtaining the fruits of *Terminalia bellerica*; (b) drying the plant part of step a in shade; (c) forming the dried plant material of step 'b' into powdered dried plant material; (d) extracting the powdered dried plant material of step 'c' withorganic solvents (preferably 50% etahanol) in the temperature range of 25-35° C.; (e) concentrating the extract obtained in step 'd' under reduced pressure at a temperature in the range of about 40-60° C.; (f) obtaining a dried extract by lyophilizing the concentrated extract for complete removal of solvent; (g) further mixing the dried extract with starch paste or other pharmacologically acceptable binder (h) exogenously adding a mixture of malonic acid (0.5-2% w/w), glutamic acid (2-4% w/w), eicosenoic acid (4-5% w/w) and linolenic acid (2-4% w/w) to the composition formed in 'g'.

In an embodiment of the invention wherein the composition wherein the said composition comprises about 9.5-20% wt/wt of *T. bellerica* dried fruit extract along with organic acids and binders comprise 80%-90.5% wt/wt of the total formulation.

In an embodiment of the invention wherein the composition wherein in the step 'g' the said binder is selected from a group consisting of starch, starch paste, gum acacia or carboxy methyl cellulose.

Accordingly, a herbal composition is useful for curing gastro intestinal infections comprising of fruits of *Terminalia bellerica*, more particularly extracts of fruits, and exogenously added malonic acid, glutamic acid, eicosenoic acid and linolenic acid which can be used for the effective cure of gastro intestinal problems.

DETAILED DESCRIPTION OF THE INVENTION

*Terminalia bellerica* is a traditionally known to possess various medicinal properties. The fruits of *T. bellerica* are one of the constituents for the Ayurvedic 'Triphala'. In view of the extensive usage of this plant in different medicare systems, the fruits of *T. bellerica* were taken to test its efficacy in treating gastro intestinal problems. The fruits were taken from the CSIR-NBRI garden in the month of May-June and shade dried to ensure loss of moisture so that it could be grinded into a dry powder form.

Preparation of Herbal Formulation:

The fruits of *Terminalia bellerica* (1-5% w/w) were dried in shade, powdered and extracted with organic solvents (preferably 50% ethanol), the dried fruit powder and solvent being in the ratio 1:3, for 5 days. At the end of this the solvent was decanted and filtered to remove plant debris.

The extract was then concentrated under vacuum at less than 50° C. The extract was then lyophilized to obtain the extract in powder form. The extract is further mixed with starch paste and processed to semisolid water soluble mixture. Another mixture of malonic acid (0.5-2% w/w), glutamic acid (2-4% w/w), eicosenoic acid (4-5% w/w) and linolenic acid (2-4% w/w) was added exogenously to the above mixture to form a mass. The mass is then granulated in a granulator, dried at 104° F. and screened through 16 mesh screens. The dried granules were further mixed with the inert natural binders in sufficient quantity to make 100%. The composition thus prepared, formed an easily acceptable solid dosage form. The composition can also be processed to a liquid dosage form using syrup as per the British pharmacopoeia. Thus it can be used as a solid or liquid dosage form.

For the present invention, effect of the formulation on normal defecation was evaluated to ensure that it does not cause diarrhea. Five groups of six rats each were placed individually in separate cages with filter papers at the bottom. The doses of the extracts were administered orally to different groups. The nonspecific antidiarrheal reference drug diphenoxylate HCl (5.0 mg kg$^{-1}$, p.o.) and 1% CMC (10 mg kg$^{-1}$, p.o.) were administered to two groups and later served as controls. The total number of the faecal matter in each group was assessed every hour for the next 4 h. Percent reduction in the total number of faeces in the treated groups was obtained by comparison with control animals. The result suggested that the formulation does not cause diarrhea to the experimental animals.

The efficacy of composition as an antidiarrheal agent was evaluated using castor oil induced diarrhea. The castor oil model has been an extensively used pharmacological test to screen and evaluate antidiarrheal properties of drugs in rats. The liberation of ricinoleic acid from castor oil results in irritation and inflammation of intestinal mucosa, leading to release of prostaglandins, which stimulates motility and secretion (Pierce, N. F., Carpenter. C. C. J., Elliiot, H. Z. and Greenough, W. B., Effects of prostaglandins, Theophylline and cholera exotoxin upon transmucosalwater and electrolyte movement in canine jejunum, Gastroenterology, 1971; 60: 22-32). Castor oil is also reported to induce diarrhea by increasing the volume of intestinal content by prevention of the reabsorption of water. The liberation of ricinoleic acid results in irritation and inflammation of intestinal mucosa, leading to release of prostaglandins which results in stimulation of secretion. Thereby prevents the reabsorption of NaCl and H2O (Galveg, J., Zavzueto, A., crespo, M. E., Lorento, M. D., oeete, M. A. and Jimenez, J., Anti-diarrheic activity of *euphorbia hirta* extract and isolation of an active flavonoid constituent, Plantamedica, 1993; 59: 333-336). In the present investigation, the rats fasted for 24 h were randomly allocated to five groups of six animals each. Group I received 1% CMC (10 ml/kg, p.o.), groups II, III and IV received orally the drug extract (50, 100 and 200 mg/kg), respectively. The group V was given diphenoxylate HCl (5.0 mg/kg, p.o.) as suspension. After 60 min each animal was given with 2 mL of castor oil by orogastric cannula, and placed in a separate cage and observed for 4 h defecation the characteristic diarrheal droppings were noted and recorded. Significant antidiarrheal effect was shown for the formulation at a concentration of 50 mg/kg.

The effect of the composition on ulcers was evaluated using aspirin induced ulcer model. Gastric ulcer is one of the most widespread disorder of the gastro intestinal tract (Alkofahi, A. and A. H. Atta, 1999. Pharmacologicalscreening of the antiulcerogenic effects of some Jordanian Mecicinal Plants in rats. J. Ethnopharmacol, 65: 341-345). When the gastric mucosa is continuously exposed topotentially injurious agents such as acid, pepsin, bile acids, bacterial products (*Helicobacter pylori*) and drugs, the gastric ulcer prevalence increases (Peskar, B. M. and N. Maricic, 1998. Role of prostaglandins in gastroprotection. Dig. Dis. Sci., 43: 523-529). Aspirin which is one of the most commonly used non-steroidal anti-inflammatory drug, is associated with gastrointestinal side effects of variable severities ranging from mild dyspepsia to fatal gastric bleeding. Aspirin leads to inhibition in the gastric mucosal protective factors and at the same time it increases the aggressive factors to which the mucosa of the stomach is exposed (Babbar N, Gemer E W, Casero R A, Jr. Induction of spermidine/spermine Ni-acetyltransferase (SSAT) by aspirin in Caco-2 colon cancer cells. Biochem J 2006; 394 (Pt 1): 317-24). In the present study, a rat model of aspirin induced gastric ulcer was used to test and compare the protective effects of an antisecretory $H_2$-receptor blocker, ranitidine and the *T. bellerica* based herbal formulation. Aspirin in dose of 200 mg/kg (20 mg/ml) was administered to the animals, which were grouped into five categories; a control group in which the ulcers weree induced, however no medication was provided; F1 group which was treated with 100 mg/kg of water soluble paste of *T. bellerica*; F2 group which was treated with the *T. bellerica* based formulation at a concentration of 25 mg/kg; F3 group which was treated with the *T. bellerica* based formulation at a concentration of 50 mg/kg and a positive control group treated with ranitidine. Ulcers were scored after 4 h. The animals were sacrificed and the stomach was then excised and cut along the greater curvature, washed carefully with 5.0 ml of 0.9% NaCl and ulcers were scored in the glandular portion of the stomach. Ulcer index was calculated by adding the total number of ulcers per stomach and the total severity of ulcers per stomach. Results of the study indicated that a 50 mg/kg concentration of the formulation produced a significant decrease in the gastric lesion score as compared to other groups.

The effect of the composition as an antiulcer agent was further justified using pylorus ligation (PL)-induced ulcer model. In pylorus ligation, the digestive effect of accumulated gastric juice and interference of gastric blood circulation are responsible for the induction of ulceration (Patel A V, Santani D D, Goel R K. Antiulcer activity and the mechanism of action of magaldrate in gastric ulceration models of rat. Indian J Physiol Pharmacol. 2000; 44:350-4). For this experiment also, the animals were categorized in five groups; a control group in which the ulcers were induced, however no medication was provided; F1 group which is treated with 100 mg/kg of water soluble paste of *T. bellerica*; F2 group which is treated with the *T. bellerica* based formulation at a concentration of 25 mg/kg; F3 group which is treated with the *T. bellerica* based formulation at a concentration of 50 mg/kg and a positive control group treated with ranitidine. The mentioned drugs were administered for a period of 5 days as described above and the rats were kept for 18 h fasting and care was taken to avoid coprophagy. Animals were anaesthetized and the abdomen was opened and pylorus ligation was done without causing any damage to its blood supply. After 4 h, stomachs were dissected out and cut open along the greater curvature and ulcers were scored in the glandular portion of the stomach as mentioned in aspirin induced ulcers. Results of the study indicated that a 50 mg/kg concentration of the formulation produced a significant decrease in the gastric lesion score as compared to other groups.

Further, effect of the composition was evaluated using ethanolinduced ulcer model. Ethanol is one of the most widely used agents in experimental models for the evaluation of drugs antiulcerative activity in rats (Akhtar A H and K U, Ahmad (1995) Antiulcerogenic evaluation of the methanolic extracts of some indigenous medicinal plants of Pakistan in aspirin-ulcerated rats, J Ethnopharmacol.; 46: 1-; Atta, A. H; Soad M. Nasr and Samar M. Mouncir (2005) Antiulcerogenic effect of some plant extracts Natural Product Radiance, 4: 258-263). The acute effect of ethanol has been proved to be due to protein precipitation of the cytoplasmatic components in the superficial cells of the gastric mucosa and release of the vasoactive mediators such as leukotrienes C4 (LTC4) and histamine (Jamal A; Kalim Javed; M, Aslama and Ma Jafri (2006) Gastroprotective effect of cardamom, Elettaria cardamomum Maton fruitsin rats J Ethnopharmacol 103: 149-153). The vasoactive mediators cause blood flow stasis in the microcirculation of the mucous membrane; an effect which may contribute to the increased lesions in this model (Konturek S J; T, Brzozowski: D. Drozdowicz and G Beck (1988) Role of leukotrienes in acute gastric lesions by ethanol, taurocholate, aspirin, platelet activating factor and stress in rats Dig Dis Sci 33:806-813; Wallace J L (2001) Mechanisms of protection and healing: current knowledge and future research Am J Med 110:19-23). In addition, alcohol may also induce solubilization in the mucous of the stomach wall, increase the flow of sodium and potassium into the lumen, increase the pepsin release, and decrease the tissue levels of DNA, RNA and proteins, which predisposes the mucous membrane unprotected, thus leading to tissue injury (Robert A; J E. Nezamis: C. Lancaster and A J Hanchar (1979) Cytoprotection by prostaglandins in rats Prevention of gastric necrosis produced by alcohol, HCl. NaOH, hypertonic NaCl and thermal injury Gastroenterology 77: 433-443). Moreover, ethanol has been proved to increases the production of reactive oxygen species (ROS) and free radicals (Gazzieri D (2007) Substance P released by TRPVI-expressing neurons produces reactive oxygen species that mediate ethanol-induced gastric injury Free Radic Biol Med, 43: 581-589).The gastric ulcers were induced in rats by administrating EtOH (1 ml/200 g, 1 h) (Hollander D. Taranawski A, Krause W J, Gergely H (1985). Protective effect of sucralfate against alcohol-induced gastric mucosal injury in the rat. Gastroenterol., 88: 366-374) and the animals were sacrificed by cervical dislocation and stomach was incised along the greater curvature and examined for ulcers. The ulcer index was scored, based upon the product of length and width of the ulcers present in the glandular portion of the stomach ($mm^2$/rat). The lesions were found to be markedly reduced in stomach of rats treated with the 50 mg/kg concentration of the formulation.

The effect of composition was further observed on cold resistant stress model of ulcer. In this model, gastric ulcer formation was mainly due to gastric hypermotility, which could lead tomucosal over friction (Qiu B S, Cho C H, Ogle C W. The influence of chronic nicotinetreatment on stress-induced gastric ulceration andemptying ratein rats. Experientia 1992; 48: 389-391). Hence, the gastric mucus layer is extremely important and the mucus is generally believed to contribute to a cytoprotective action. Gastric mucus originates from the goblet cells and NO plays a critical role in the maintenance of goblet cell functions. NO donors could increase mucus release from gastric mucosal cells in rats (Brown J F, Keates A C, Hanson P J, Whittle B J. Nitric oxide generators and cGMP stimulate mucus secretion by rat gastric mucosal cells. Am J Physiol 1993; 265: G418-422) and enhance mucus gel thickness in the rat stomach (Brown J F, Hanson P J, Whittle B J. (1992) Nitric oxide donors increase mucus gel thickness in rat stomach. Eur J Pharmacol 1992; 223: 103-104). For the experiment the rats were groups as: a control group in which the cold restraint ulcers were induced, however no medication was provided; F1 group which is treated with 100 mg/kg of water soluble paste of *T. bellerica*; F2 group which is treated with the *T. bellerica* based formulation at a concentration of 25 mg/kg; F3 group which is treated with the *T. bellerica* based formulation at a concentration of 50 mg/kg and a positive control group treated with ranitidine. Rats were starved for 48 hours, and the drinking solution was removed 1 hour before starting experiments. For cold-restraint s tress, the rats were restrained in individual close-fitting tubular wire-mesh cages at 4° C. (Qiu B S, Pfeiffer C J, Cho C H. Effects of chronic nitric oxide synthase inhibition in cold-restraint and ethanol-induced gastricmucosal damage in rats. Digestion 1996; 57: 60-66) and the no stress control group was kept in starvation cages at 22° C. At the end of 2 hours, all the rats were sacrificed. The ulcer index was scored, based upon the product of length and width of the ulcers present in the glandular portion of the stomach ($mm^2$/rat). The lesions were found to be markedly reduced in stomach of rats treated with the 50 mg/kg concentration of the formulation.

Diarrhea results from an imbalance between the absorptive and secretory mechanisms in the intestinal tract, resulting in an excess loss of fluid in the feces. In some diarrheas, the secretory component predominates, while other diarrheas are characterized by hypermotility. Castor oil is also reported to induce diarrhea by increasing the volume of intestinal content by prevention of the reabsorption of water. The liberation of ricinoleic acid results in irritation and inflammation of intestinal mucosa, leading to release of prostaglandins which results in stimulation of secretion. Thereby prevents the reabsorption of NaCl and H2O. The results of the present study showed that the *Terminalia bellerica* based herbal formulation produced a statistically significant reduction in the severity and frequency of diarrhea produced by castor oil. Ulcers develop when the normal defense and repair mechanisms of the lining of the stomach or duodenum are weakened, making the lining more likely to be damaged by gastric acid. A peptic ulcer is a score on the lining of the stomach, small intestine or esophagus (Sharma, H. and K. K. Sharma, 2008. Principles of pharmacology by Paras publication, Hyderabad, India., 1 edition, ISBN 978-81-8191-1776-6: 387-390). Effect of the formulation on various ulcer models suggested significant antiulcer potential. Thus it is concluded that the herbal based composition is effective in the cure of various gastrointestinal disorders.

The compositions of the present invention are synergistic composition and not a mere aggregation of properties of the individual components. The present invention discloses the synergistic composition comprising of exogenous organic acids in specific ratio with *T. bellerica* for the treatment of gastrointestinal problems. The composition provides surprisingly unexpected results as compared to *T. bellerica* fruits alone or the mixture of organic acids alone.

The following examples are given by way of illustrations and should not be construed to limit the scope of the invention.

Example 1

The *T. bellerica* fruits were taken from the CSIR-NBRI garden (National Botanical Research Institute) Lucknow (26° 51'29.65"N; 80° 56'59.29"E; altitude: 117 m) in the month of May-June and shade dried to ensure loss of moisture so that it could be grinded into a dry powder form.

The fruits of *Terminalia bellerica* were dried in shade and extracted with organic solvents preferably 50% ethanol, the fruit powder and organic solvent being in the ratio 1:3, for 5 days. At the end of this the solvent was decanted and filtered to remove plant debris. The extract was then concentrated under vacuum at less than 50° C. The extract was then lyophilized to obtain the extract in powder form. The extract is further mixed with tapioca starch paste and processed to semisolid water soluble mixture. Another mixture of malonic acid, glutamic acid, eicosenoic acid and linolenic acid was added exogenously to the above mixture to form a mass. The mass is then granulated in a granulator, dried at 104° F. and screened through 16 mesh screens. The dried granules were further mixed with the tapioca starch paste in sufficient quantity to make 100%. The composition thus prepared, formed an easily acceptable solid dosage form. The composition can also be processed to a liquid dosage form using syrup as per the British pharmacopoeia. Thus it can be used as a solid or liquid dosage form. The formulation A given below is useful for the treatment of various gastro intestinal disorders.

Preparation of Tapioca Starch Paste:

The root tubers of cassava were purchased from local market of Lucknow, Uttar Pradesh, India. The starch was extracted from root tubers of cassava (*Manihot esculenta*). Cassava tubers were peeled, washed and cut to small pieces. These small pieces were then soaked in distilled water for specified period of time i.e. for 1 h. At the end of the steeping period, the softened tubers were milled to a pulp, and more distilled water was added to give dilute slurry which was sieved using mesh size 100 (Patel Shailendra, Agrawal Shikha, Lodhi Bhekam Singh. International Journal of Pharmaceutical & Biological Archives 2012; 3(3):466-473).

In the process in place of tapioca starch other inert binders may be used.

The biological activity data with reference to the synergistic activity data is presented for proof of evidence linked the examples are given below:

Example 2. Formulation A (Prepared by the Process of Example 1)

Dried Extract of *T. bellerica* Fruits (4.5% w/w)
Malonic acid (0.5% w/w)
Glutamic acid (2% w/w)
Eicosenoic acid (4% w/w)
Linolenic acid (2.5% w/w)
Tapioca starch (binder) (86.5%)
Biological Activity:

The castor oil model has been an extensively used pharmacological test to screen and evaluate antidiarrheal properties of drugs in rats. The liberation of ricinoleic acid from castor oil results in irritation and inflammation of intestinal mucosa, leading to release of prostaglandins, which stimulates motility and secretion (Pierce, N. F., Carpenter. C. C. J., Elliiot, H. Z. and Greenough, W. B., Effects of prostaglandins, Theophylline and cholera exotoxin upon transmucosalwater and electrolyte movement in canine jejunum, Gastroenterology, 1971; 60: 22-32). Castor oil is also reported to induce diarrhea by increasing the volume of intestinal content by prevention of the reabsorption of water. The liberation of ricinoleic acid results in irritation and inflammation of intestinal mucosa, leading to release of prostaglandins which results in stimulation of secretion. Thereby prevents the reabsorption of NaCl and H2O (Galveg, J., Zavzueto, A., crespo, M. E., Lorento, M. D., oeete, M. A. and Jimenez, J., Anti-diarrheic activity of *euphorbia hirta* extract and isolation of an active flavonoid constituent, Plantamedica, 1993; 59: 333-336). In the present investigation, the rats fasted for 24 h were randomly allocated to five groups of six animals each. Group I received 1% CMC (10 ml/kg, p.o.), groups II, III and IV received orally the drug extract (50, 100 and 200 mg/kg), respectively. The group V was given diphenoxylate HCl (5.0 mg/kg, p.o.) as suspension. After 60 min each animal was given with 2 mL of castor oil by orogastric cannula, and placed in a separate cage and observed for 4 h defecation the characteristic diarrheal droppings were noted and recorded.

TABLE 1

Effect of formulation on castor-oil induced diarrhea

| Treatment | Total number of faecal matter |
|---|---|
| Control | 65 |
| F1 | 43 |
| F2 | 52 |
| F3 | 31 |
| F4 | 18 |
| DiphenoxylateHCl | 19 |

F1: Semi solid water soluble extract of *Terminalia bellerica* 100 mg/kg
F2: Mixture of malonic acid (0.5% w/w), glutamic acid (2% w/w), eicosenoic acid (4% w/w), linolenic acid (2.5% w/w)
F3: *Terminalia bellerica* (4.5% w/w) with malonic acid (0.5% w/w), glutamic acid (2% w/w), eicosenoic acid (4% w/w)and linolenic acid (2.5% w/w) at 25 mg/kg
F4: *Terminaliabellerica*(4.5% w/w) with malonic acid (0.5% w/w), glutamic acid (2% w/w), eicosenoic acid (4% w/w)and linolenic acid (2.5% w/w) at 50 mg/kg The study showed the antidiarrheal effect of *T. bellerica* extract (4.5%) alone (F1); the mixture of organic acids alone (F2) and the composition as mentioned in Formulation A (F3 & F4). F4 shows significantly higher antidiarrheal activity. The composition showed higher antidiarrheal activity as compared to the commercially available antidiarrheal salt, DiphenoxylateHCl.

Example 3. Formulation B

Dried extract of *Terminalia bellerica* fruits (5% w/w) (Prepared by the process of example 1)
Malonic acid (1% w/w)
Glutamic acid (2% w/w)
Eicosenoic acid (5% w/w)
Linolenic acid (2.5% w/w)
Tapioca starch (binder) (84.5%)
Biological Activity:

The effect of composition was further observed on cold resistant stress model of ulcer. In this model, gastric ulcer formation was mainly due to gastric hypermotility, which could lead tomucosal over friction (Qiu B S, Cho C H, Ogle C W. The influence of chronic nicotinetreatment on stress-induced gastric ulceration andemptying ratein rats. Experientia 1992; 48: 389-391). Hence, the gastric mucus layer is extremely important and the mucus is generally believed to contribute to a cytoprotective action. Gastric mucus originates from the goblet cells and NO plays a critical role in the maintenance of goblet cell functions. NO donors could increase mucus release from gastric mucosal cells in rats (Brown J F, Keates A C, Hanson P J, Whittle B J. Nitric oxide generators and cGMP stimulate mucus secretion by rat gastric mucosal cells. Am J Physiol 1993; 265: G418-422) and enhance mucus gel thickness in the rat stomach (Brown J F, Hanson P J, Whittle B J. (1992) Nitric oxide donors increase mucus gel thickness in rat stomach. Eur J Pharmacol 1992; 223: 103-104). For the experiment the rats were groups as: a control group in which the cold restraint ulcers were induced, however no medication was provided; F1 group which is treated with 100 mg/kg of water soluble paste of *T. bellerica*; F2 group which is treated with the *T. bellerica* based formulation at a concentration of 25 mg/kg; F3 group which is treated with the *T. bellerica* based formulation at a concentration of 50 mg/kg and a positive control group treated with ranitidine. Rats were starved for 48 hours, and the drinking solution was removed 1 hour before starting experiments. For cold-restraint stress, the rats were restrained in individual close-fitting tubular wire-mesh cages at 4° C. (Qiu B S, Pfeiffer C J, Cho C H. Effects of chronic nitric oxide synthase inhibition in cold-restraint and ethanol-induced gastricmucosal damage in rats. Digestion 1996; 57: 60-66) and the no stress control group was kept in starvation cages at 22° C. At the end of 2 hours, all the rats were sacrificed. The ulcer index was scored, based upon the product of length and width of the ulcers present in the glandular portion of the stomach ($mm^2$/rat).

TABLE 2a

Effect of formulation on cold restrained stress (CRS) induced ulcers in rats

| Treatment | Ulcer Index |
|---|---|
| Control | 21.3 ± 3.7 |
| F1 | 19.3 ± 1.4 |
| F2 | 18.2 ± 2.8 |
| F3 | 14.5 ± 2.2$^a$ |
| F4 | 1.6 ± 1.1$^c$ |
| Ranitidine 50 | 6.9 ± 1.0$^c$ |

Values are mean ± SEM for six rats.
P: $^a$<0.05, $^b$<0.01 and $^c$<0.001 compared to respective control group.
F1: Semi solid water soluble extract of *Terminalia bellerica* 100 mg/kg
F2: Mixture of malonic acid (1% w/w), glutamic acid (2% w/w), eicosenoic acid (5% w/w), linoleic acid (2.5% w/w)
F3: *Terminalia bellerica* (5%) with malonic acid (1 wt. %,), glutamic acid (2%), eicosenoic acid (5%) and linolenic acid (2.5%) at 25 mg/kg
F4: *Terminaliabellerica*(5%) with malonic acid (1%,), glutamic acid (2%), eicosenoic acid (5%) and linolenic acid (2.5%) at 50 mg/kg.

Explanation:

The above mentioned formulation is effective in curing cold restrained stress (CRS) induced ulcer. The study showed significantly high antiulcer activity as compared to the commercially available Ranitidine. Also the composition is more effective than the *T. bellerica* extract alone (F1) or the mixture of acids alone (F2).

Example 4. Formulation 3 (Prepared by the Process of Example 1)

Dried extract of *Terminalia bellerica* fruits (3.5% w/w)
Malonic acid (0.5% w/w)
Glutamic acid (2.5% w/w)
Eicosenoic acid (4.5% w/w)
Linolenic acid (2% w/w)
Tapioca starch (binder) (87%)
Biological Activity:

The effect of the composition on ulcers was evaluated using aspirin induced ulcer model. Gastric ulcer is one of the most widespread disorder of the gastro intestinal tract (Alkofahi, A. and A. H. Atta, 1999. Pharmacological screening of the antiulcerogenic effects of some Jordanian Medicinal Plants in rats. J. Ethnopharmacol, 65: 341-345). When the gastric mucosa is continuously exposed topotentially injurious agents such as acid, pepsin, bile acids, bacterial products (*Helicobacter pylori*) and drugs, the gastric ulcer prevalence increases (Peskar, B. M. and N. Maricic, 1998. Role of prostaglandins in gastro protection. Dig. Dis. Sci., 43: 523-529). Aspirin which is one of the most commonly used non-steroidal anti-inflammatory drug, is associated with gastrointestinal side effects of variable severities ranging from mild dyspepsia to fatal gastric bleeding. Aspirin leads to inhibition in the gastric mucosal protective factors and at the same time it increases the aggressive factors to which the mucosa of the stomach is exposed (Babbar N, Gerner E W, Casero R A, Jr. Induction of spermidine/spermine Ni-acetyltransferase (SSAT) by aspirin in Caco-2 colon cancer cells. Biochem J 2006; 394 (Pt 1): 317-24). In the present study, a rat model of aspirin induced gastric ulcer was used to test and compare the protective effects of an antisecretory $H_2$-receptor blocker, ranitidine and the *T. bellerica* based herbal formulation. Aspirin in dose of 200 mg/kg (20 mg/ml) was administered to the animals, which were grouped into five categories; a control group in which the ulcers weree induced, however no medication was provided; F1 group which was treated with 100 mg/kg of water soluble paste of *T. bellerica*; F2 group which was treated with the *T. bellerica* based formulation at a concentration of 25 mg/kg; F3 group which was treated with the *T. bellerica* based formulation at a concentration of 50 mg/kg and a positive control group treated with ranitidine. Ulcers were scored after 4 h. The animals were sacrificed and the stomach was then excised and cut along the greater curvature, washed carefully with 5.0 ml of 0.9% NaCl and ulcers were scored in the glandular portion of the stomach. Ulcer index was calculated by adding the total number of ulcers per stomach and the total severity of ulcers per stomach.

TABLE 2b

Effect of formulation on aspirin induced ulcers in rats

| Treatment | Ulcer Index |
|---|---|
| Control | 18.4 ± 4.6 |
| F1 | 12.1 ± 2.0 |
| F2 | 13.24 ± 3.8 |
| F3 | 10.0 ± 1.3 |
| F4 | 0.3 ± 1.2$^a$ |
| Ranitidine 50 | 7.6 ± 1.4$^a$ |

Values are mean ± SEM for six rats.
P: $^a$<0.05, $^b$<0.01 and $^c$<0.001 compared to respective control group.
F1: Semi solid water soluble extract of *Terminalia bellerica* 100 mg/kg
F2: Mixture of malonic acid (0.5% w/w), glutamic acid (2.5% w/w), eicosenoic acid (4.5% w/w), linolenic acid (2% w/w)
F3: *Terminalia bellerica* (3.5%) with malonic acid (0.5.%), glutamic acid (2.5%), eicosenoic acid (4.5%) and linolenic acid (2%) at 25 mg/kg
F4*Terminaliabellerica*(3.5%) with malonic acid (0.5%,), glutamic acid (2.5%), eicosenoic acid (4.5%) and linolenic acid (2%) at 50 mg/kg The above mentioned formulation is effective in curing aspirin induced ulcer. The study showed significantly high antiulcer activity as compared to the commercially available Ranitidine. Also the composition is more effective than the *T. bellerica* extract alone (F1) or the mixture of acids alone (F2).

Example 5. Formulation 4 (Prepared by the Process of Example 1)

Dried extract of *Terminalia bellerica* fruits (4.5% w/w)
Malonic acid (0.5% w/w)
Glutamic acid (2.5% w/w)
Eicosenoic acid (4% w/w)
Linolenic acid (2.5% w/w)
Tapioca starch (binder) (86%)

Biological Activity:

The effect of the composition as an antiulcer agent was further justified using pylorus ligation (PL)-induced ulcer model. In pylorus ligation, the digestive effect of accumulated gastric juice and interference of gastric blood circulation are responsible for the induction of ulceration (Patel A V, Santani D D, Goel R K. Antiulcer activity and the mechanism of action of magaldrate in gastric ulceration models of rat. Indian J Physiol Pharmacol. 2000; 44:350-4). For this experiment also, the animals were categorized in five groups; a control group in which the ulcers were induced, however no medication was provided; F1 group which is treated with 100 mg/kg of water soluble paste of T. bellerica; F2 group which is treated with the T. bellerica based formulation at a concentration of 25 mg/kg; F3 group which is treated with the T. bellerica based formulation at a concentration of 50 mg/kg and a positive control group treated with ranitidine.

The mentioned drugs were administered for a period of 5 days as described above and the rats were kept for 18 h fasting and care was taken to avoid coprophagy. Animals were anaesthetized and the abdomen was opened and pylorus ligation was done without causing any damage to its blood supply. After 4 h, stomachs were dissected out and cut open along the greater curvature and ulcers were scored in the glandular portion of the stomach as mentioned in aspirin induced ulcers.

TABLE 2c

Effect of formulation on pylorus ligation induced ulcers in rats

| Treatment | Ulcer Index |
|---|---|
| Control | 11.5 ± 2.5 |
| F1 | 10.4 ± 2.6 |
| F2 | 10.1 ± 3.2 |
| F3 | 9.0 ± 2.11 |
| F4 | 3.0 ± 1.2$^a$ |
| Ranitidine 50 | 4.9 ± 1.3$^b$ |

Values are mean ± SEM for six rats.
P: $^a$<0.05, $^b$<0.01 and $^c$<0.001 compared to respective control group.
F1: Semi solid water soluble extract of Terminalia bellerica 100 mg/kg
F2: Mixture of malonic acid (0.5% w/w), glutamic acid (2.5% w/w), eicosenoic acid (4% w/w), linolenic acid (2.5% w/w)
F3: Terminalia bellerica (4.5%) with malonic acid (0.5%), glutamic acid (2.5%), eicosenoic acid (4%) and linolenic acid (2.5%) at 25 mg/kg
F4 Terminalia bellerica(4.5%) with malonic acid (0.5%,), glutamic acid (2.5%), eicosenoic acid (4%) and linolenic acid (2.5%) at 50 mg/kg.

The above mentioned formulation is effective in curing pylorus ligation induced ulcer. The study showed significantly high antiulcer activity as compared to the commercially available Ranitidine. Also the composition is more effective than the T. bellerica extract alone (F1) or the mixture of acids alone (F2).

Example 6. Formulation 5 (Prepared by the Process of Example 1)

Dried extract of Terminalia bellerica fruits (5% w:w)
Malonic acid (1% w/w)
Glutamic acid (3% w/w)
Eicosenoic acid (4.5% w/w)
Linolenic acid (3% w/w)
Tapioca starch (binder) (83.5)
Biological Activity:

Ethanol is one of the most widely used agents in experimental models for the evaluation of drugs antiulcerative activity in rats (Akhtar A H and KU, Ahmad (1995) Antiulcerogenic evaluation of the methanolic extracts of some indigenous medicinal plants of Pakistan in aspirin-ulcerated rats, J Ethnopharmacol.; 46: 1-; Atta, A. H; Soad M. Nasr and Samar M. Mouneir (2005) Antiulcerogenic effect of some plant extracts Natural Product Radiance, 4: 258-263). The acute effect of ethanol has been proved to be due to protein precipitation of the cytoplasmatic components in the superficial cells of the gastric mucosa and release of the vasoactive mediators such as leukotrienes C4 (LTC4) and histamine (Jamal A; Kalim Javed; M, Aslama and Ma Jafri (2006) Gastroprotective effect of cardamom, Elettaria cardamomum Maton fruitsin rats J Ethnopharmacol 103: 149-153). The vasoactive mediators cause blood flow stasis in the microcirculation of the mucous membrane; an effect which may contribute to the increased lesions in this model (Konturek S J; T, Brzozowski: D, Drozdowicz and G Beck (1988) Role of leukotrienes in acute gastric lesions by ethanol, taurocholate, aspirin, platelet activating factor and stress in rats Dig Dis Sci 33:806-813; Wallace J L (2001) Mechanisms of protection and healing: current knowledge and future research Am J Med 110:19-23). In addition, alcohol may also induce solubilization in the mucous of the stomach wall, increase the flow of sodium and potassium into the lumen, increase the pepsin release, and decrease the tissue levels of DNA, RNA and proteins, which predisposes the mucous membrane unprotected, thus leading to tissue injury (Robert A; J E. Nezamis: C. Lancaster and A J Hanchar (1979) Cytoprotection by prostaglandins in rats Prevention of gastric necrosis produced by alcohol, HCl. NaOH, hypertonic NaCl and thermal injury Gastroenterology 77: 433-443). Moreover, ethanol has been proved to increases the production of reactive oxygen species (ROS) and free radicals (Gazzieri D (2007) Substance P released by TRPVI-expressing neurons produces reactive oxygen species that mediate ethanol-induced gastric injury Free Radic Biol Med, 43: 581-589).The gastric ulcers were induced in rats by administrating EtOH (1 ml/200 g, 1 h) (Hollander D. Taranawski A, Krause W J, Gergely H (1985). Protective effect of sucralfate against alcohol-induced gastric mucosal injury in the rat. Gastroenterol., 88: 366-374) and the animals were sacrificed by cervical dislocation and stomach was incised along the greater curvature and examined for ulcers. The ulcer index was scored, based upon the product of length and width of the ulcers present in the glandular portion of the stomach ($mm^2$/rat).

TABLE 2d

Effect of formulation on ethanol induced ulcers in rats

| Treatment | Ulcer Index |
|---|---|
| Control | 20.2 ± 5.0 |
| F1 | 21.0 ± 5.1 |
| F2 | 21.8 ± 6.2 |
| F3 | 11.5 ± 4.2 |
| F4 | 2.3 ± 2.5$^a$ |
| Ranitidine 50 | 10.3 ± 2.8$^a$ |

Values are mean ± SEM for six rats.
P: $^a$<0.05, $^b$<0.01 and $^c$<0.001 compared to respective control group.
F1: Semi solid water soluble extract of Terminaliabellerica 100 mg/kg
F2: Mixture of malonic acid (1% w/w), glutamic acid (3% w/w), eicosenoic acid (4.5% w/w), linolenic acid (3% w/w)
F3: Terminalia bellerica (5%) with malonic acid (1%), glutamic acid (3%), eicosenoic acid (4.5 w/w %) and linolenic acid (3%) at 25 mg/kg
F4 Terminalia bellerica(5%) with malonic acid (1%,), glutamic acid (3%), eicosenoic acid (4.5%) and linolenic acid (3%) at 50 mg/kg The above mentioned formulation is effective in curing ethanol induced ulcer. The study showed significantly high antiulcer activity as compared to the commercially available Ranitidine. Also the composition is more effective than the *T. bellerica* extract alone (F1) or the mixture of acids alone (F2).

Advantages

1. The major advantage of the formulation is that it is a herbal based composition.
2. Another advantage is that the formulation is effective in the cure of diarrhea as well as ulcers which are the two most common gastro intestinal problems.
3. The ingredients of the formulation are cost effective and readily available.

We claim:

1. A composition for the treatment of gastrointestinal disorders comprising:
   1-5 wt % *Terminalia bellerica;*
   0.5-2 wt % malonic acid;
   4-5 wt %, eicosenoic acid;
   2-4 wt % inolenic acid; and
   80-90.5 wt % binder.

2. The composition according to claim 1, wherein the *Terminalia bellerica* comprises fruits of *Terminalia bellerica*.

3. The composition according to claim 1, wherein the *Terminalia bellerica* comprises dried fruits of *Terminalia bellerica*.

4. The composition according to claim 1, wherein the *Terminalia bellerica* comprises an organic extract of dried fruits of *Terminalia bellerica*.

5. The composition according to claim 1 wherein the gastrointestinal disorders comprise diarrhea, ulcer, stomach inflammation, dysentery, gastric ulcer, duodenal ulcer, stomach ache, irritable bowel syndrome.

6. The composition according to claim 4 wherein the organic extract is a 50% ethanolic extract of the dried fruits of *Terminalia bellerica*.

* * * * *